United States Patent [19]

Lundt

[11] Patent Number: 5,766,264
[45] Date of Patent: Jun. 16, 1998

[54] MULTI-AXIS PROSTHETIC ANKLE JOINT

[75] Inventor: Judd E. Lundt, Hermosa Beach, Calif.

[73] Assignee: United States Manufacturing Company, Pasadena, Calif.

[21] Appl. No.: 705,658

[22] Filed: Aug. 30, 1996

[51] Int. Cl.$^6$ .................................................. A61F 2/64
[52] U.S. Cl. ................................................ 623/47; 623/50
[58] Field of Search ................................ 623/47, 48, 49, 623/50, 52

[56] References Cited

U.S. PATENT DOCUMENTS

| 53,931 | 4/1866 | Weston | 623/48 |
|---|---|---|---|
| 292,800 | 2/1884 | Furrer | 623/52 |
| 4,364,128 | 12/1982 | Mummert | 623/50 |
| 4,395,783 | 8/1983 | Eyre | 623/47 |
| 4,605,417 | 8/1986 | Fleishauer | 623/49 |
| 5,019,109 | 5/1991 | Voisin | 623/52 |
| 5,258,038 | 11/1993 | Robinson | 623/47 |
| 5,482,513 | 1/1996 | Wilson | 623/47 |
| 5,545,234 | 8/1996 | Collier | 623/49 |

OTHER PUBLICATIONS

Voisin, Jerome P., Dual–Ankle Springs, Multi–Axial Rotation System, D.A.S. M.A.R.S.™, Acadian Prosthetics & Orthopedic Aids, Inc.

Endolite 'Multiflex', Foot and Ankle Combination, Foot and Ladies Multiflex, Endolite North America , Certificate No. FM29097, ISO9001, EN46001.

Improved Multiflex Foot and Ankle, 509153–509170, Blatchford Endolite, Chas. A. Blatchford & Sons Ltd., Blatchford: 934609, Issue 03/0093.

OWW Single Axis Foot, Ohio Willow Food Company, PH–1065–A, Oct. 1,1994.

Primary Examiner—Michael J. Milano
Attorney, Agent, or Firm—Christie, Parker & Hale, LLP

[57] ABSTRACT

A multi-axis prosthetic ankle joint comprising a housing having a bottom portion and a top portion having a front bumper and rear bumper positioned within the housing between the bottom portion and the top portion. The front and rear bumpers and the top and bottom portions of the housing each contain at least one flange which are overlapping and include an axially aligned hole for receipt of a pin. The holes in the upper housing flanges are elongated to provide multiple axes of motion for the ankle joint. The ankle joint is adapted to be rigidly connected between a lower leg component and a foot component.

12 Claims, 3 Drawing Sheets

MULTI-AXIS PROSTHETIC ANKLE JOINT

FIELD OF THE INVENTION

This invention relates generally to prosthetic devices, and more particularly, to a universal multi-axis ankle joint comprising front and back polyurethane bumpers of different densities positioned within a metal housing for connection between a lower leg component and a foot component which provides multiple axes of rotation for the ankle.

BACKGROUND OF THE INVENTION

For smooth walking across uneven ground, it is important for an amputee to have a prosthesis capable of providing a full range of motion for the foot component with respect to the lower leg component. A full range of motion is accomplished by the use of a multiple axes of rotation ankle joint. Prior prosthetic devices provided a lower leg component having an integral foot component without provision for an ankle joint. This type of prosthesis made it difficult for the amputee to maneuver on relatively even ground, much less on uneven ground. Recognizing this problem, prosthetic foot components were developed which provided a single axis of rotation. These prosthetic feet typically included adjustable anterior and posterior deflection bumpers for transition from plantar flexion to dorsiflexion. The single axis of rotation ankle joint is integral with the foot component. The disadvantages of this design is that, although being an improvement over designs with no axis of rotation, it does not provide stability on uneven ground.

Recognizing the need for a multiple axes of rotation ankle joint, a prosthetic foot and ankle combination manufactured by Blatchford Endolite under the tradename "Multiflex" was developed to provide a full range of natural action. This design includes a ball and socket ankle joint integrally connected to the foot component through a serrated connection. A disadvantage with this type of design is that it is not universally adaptable for use between any manufacturer's lower leg and foot component. Other disadvantages of this design is that the ankle component is quite large, requires a special serrated adapter for attachment to the foot, and is expensive to manufacture.

Consequently, a need exists for an improved multiple axes prosthetic ankle component which is universally adaptable between any manufacturer's lower leg and foot components, and is compact, lightweight, and inexpensive to manufacture.

SUMMARY OF THE INVENTION

The present invention provides a multiple axes prosthetic ankle joint for lower limb prosthetic application which reduces the problems of prior existing multiple axes ankle components and is lightweight, universally adaptable for most lower leg components, and is easy and inexpensive to manufacture.

In a preferred embodiment, the multiple axes ankle joint comprises a metal housing including a bottom portion which can be positioned on or within a foot component and a top portion having a prosthetic link for connection to a lower leg component. Two polyurethane dampeners are positioned within the housing between the upper and lower portions and comprise a front bumper and a rear bumper. The front bumper has a higher durometer hardness than the rear bumper to act as a stop in the mid-stance position. The exact durometer hardness for both the front and rear bumpers can be varied depending upon the weight and activity level of the amputee.

The upper and lower portion of the housing, and the front and rear dampeners all include overlapping flanges having a hole passing therethrough. When the ankle joint is assembled, the holes are aligned for the passage of a pin for firmly connecting the ankle components together. The holes passing through the flanges on the upper housing member are elongated to also accommodate inversion and eversion motion as well as compression of the ankle. The lower portion of the housing also includes a hole through the bottom surface so the ankle joint can be bolted to the foot component. The front and rear bumpers also include a vertical hole for insertion of a plastic cylindrical limiter of varying lengths to further limit motion and to "tune" the amount of potential motion for the ankle joint.

These and other aspects of the invention will be more fully described in the following detailed description and the accompanying drawings.

Brief Description of the Drawings FIGS. 1 is a perspective view of the multiple axis ankle joint of the present invention;

DETAILED DESCRIPTION

Figure 1:
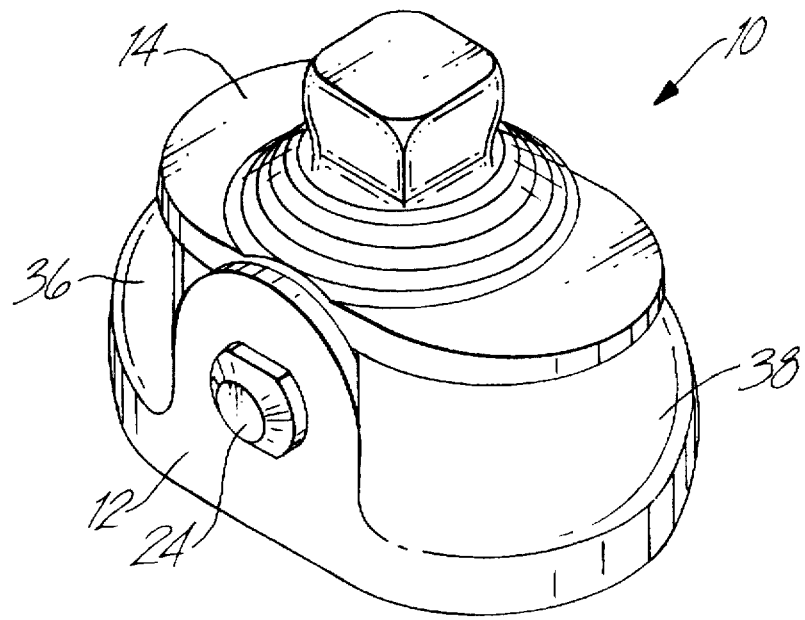
Figure 2A:
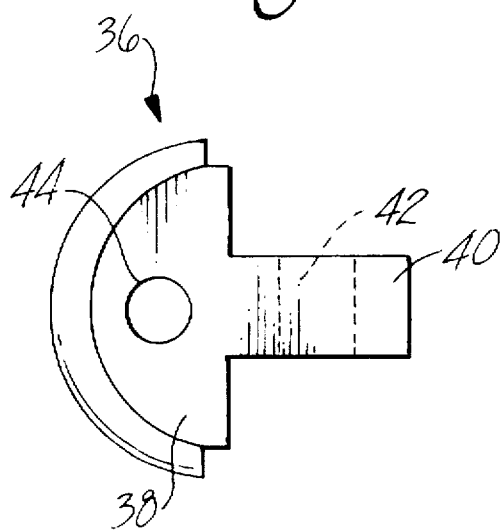
FIGS. 2a is a top view of the front damper of the ankle joint of FIG. 1.
Figure 2B:
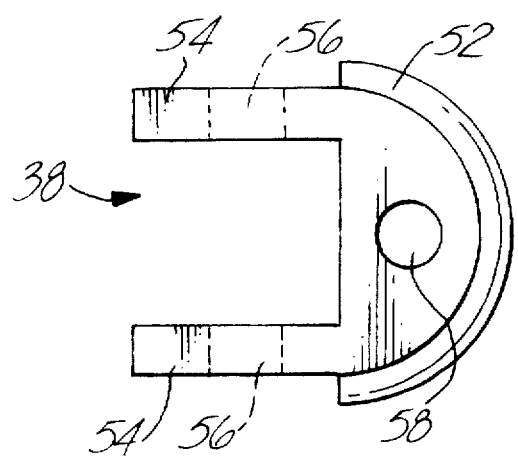
FIGS. 2b is a top view of the rear damper of the ankle joint of FIG. 1.
Figure 2:
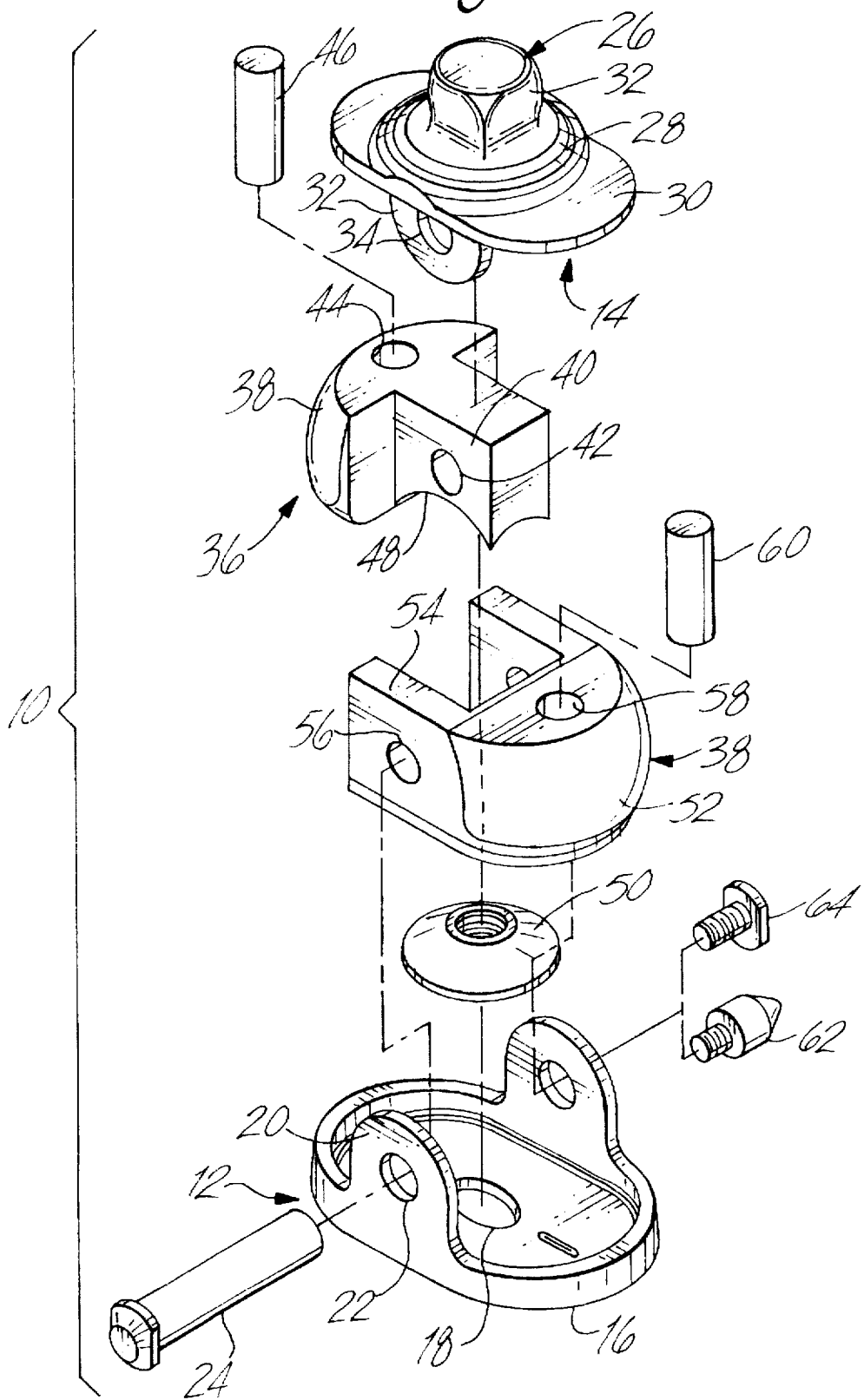
FIGS. 2 is an exploded side elevational view of the ankle joint of FIG. 1.

FIGS. 1 and 2 illustrate the multi-axis prosthetic ankle joint 10 of the present invention. The ankle joint comprises a metal housing including a bottom portion 12 and a top portion 14. The bottom portion of the housing has a cup-shaped base 16 having a hole 18 positioned in its bottom surface for connecting the ankle joint to a foot component. The bottom portion further includes vertical flanges 20, one extending upwardly on either side of the bottom portion (only one is shown in the drawing). Flanges 20 have a hole 22 for passage of a pin 24 which rigidly secures all of the components of the ankle joint together as discussed more fully herein.

Top housing portion 14 includes a prosthetic link which includes a male connector 26 having a spherically convex base 28 rigid with a generally flat plate 30. The male connector includes a central boss 32 of frustopyramidal configuration which projects upwardly away from the spherically convex base. The frustopyramid formed by the main portion of the boss is of square crosssection and has four uniform sides facing angularly upwardly and outwardly in four directions spaced apart by 90°. Positioned on the lower surface of the base 30 are two downwardly extending flanges 32 (only one shown) having an oval-shaped hole 34 for passage of pin 24. Holes 34 are elongated to accommodate plantar and dorsiflexion, inversion and eversion motion as well as compression of the ankle to be discussed more fully herein.

Two polyurethane dampeners are positioned within the housing between the bottom portion 12 and the top portion 14 and comprise a front bumper 36 and a rear bumper 38. As also shown in FIGS. 2a, front bumper 36 is T-shaped having a rounded front portion 38 and a perpendicularly extending rear portion 40. Rear portion 40 includes a horizontally extending hole 42 for passage of pin 24. Front portion 38 includes a vertically extending hole 44 for insertion of a cylindrical plastic limiter 46 to further control compression of the front bumper. The bottom surface 48 of rear portion 40 is semi-circular for receipt of a threaded washer 50 positioned within the bottom portion of the housing and extending through hole 18.

Rear bumper 38, as also shown in FIGS. 2b, is generally U-shaped having a rounded rear portion 52 and two perpendicularly extending flanges 54. Flanges 54 include a horizontally extending hole 56 for passage of pin 24. Rear portion 52 includes a vertically extending hole 58 for a plastic cylindrical limiter 60 similar to limiter 46. The length of limiters 46 and 60 can be varied to adjust their function. When the front and rear bumpers are assembled within the housing, flange 40 of the front bumper extend between flanges 54 of the rear bumper such that holes 42 and 56 are aligned with holes 22 and 34 of the bottom and top portions of the housing, respectively.

The front bumper has a higher durometer hardness than the rear bumper such that the front bumper can act as a stop in the mid-stance position. The exact durometer hardness for both the front and rear bumpers can be varied depending upon the weight and activity level of the amputee. It is further contemplated that a number of rear bumpers having a variety of hardnesses would be supplied with the ankle joint so that the prosthetist can easily change the bumper depending upon the amputer's anticipated activity level. By way of a non-limiting example, the front bumper has a shore A 95 hardness and the rear bumper would include a set of bumpers having shore A 85, shore A 75, and shore A 60 hardnesses. Preferably, the bumpers would be color coded for their varying hardnesses.

The ankle joint is assembled by positioning the front and rear bumpers within the bottom portion of the housing, and the upper portion of the housing would be positioned on top of the bumpers such that flanges 32 would be positioned between flanges 54 of the rear bumper and flange 40 of the front bumper. Then pin 24 would be passed through axially aligned holes 22, 56, 34, and 42. To aid in insertion of the pin, a bullet-shaped adapter 62 can be threaded into the end of the pin to help align the holes through the flanges of the components. Once the pin has passed entirely through the ankle joint, the adapter 62 can be unscrewed and the threaded bolt 64 would be screwed into the end of the pin.

Figure 3:
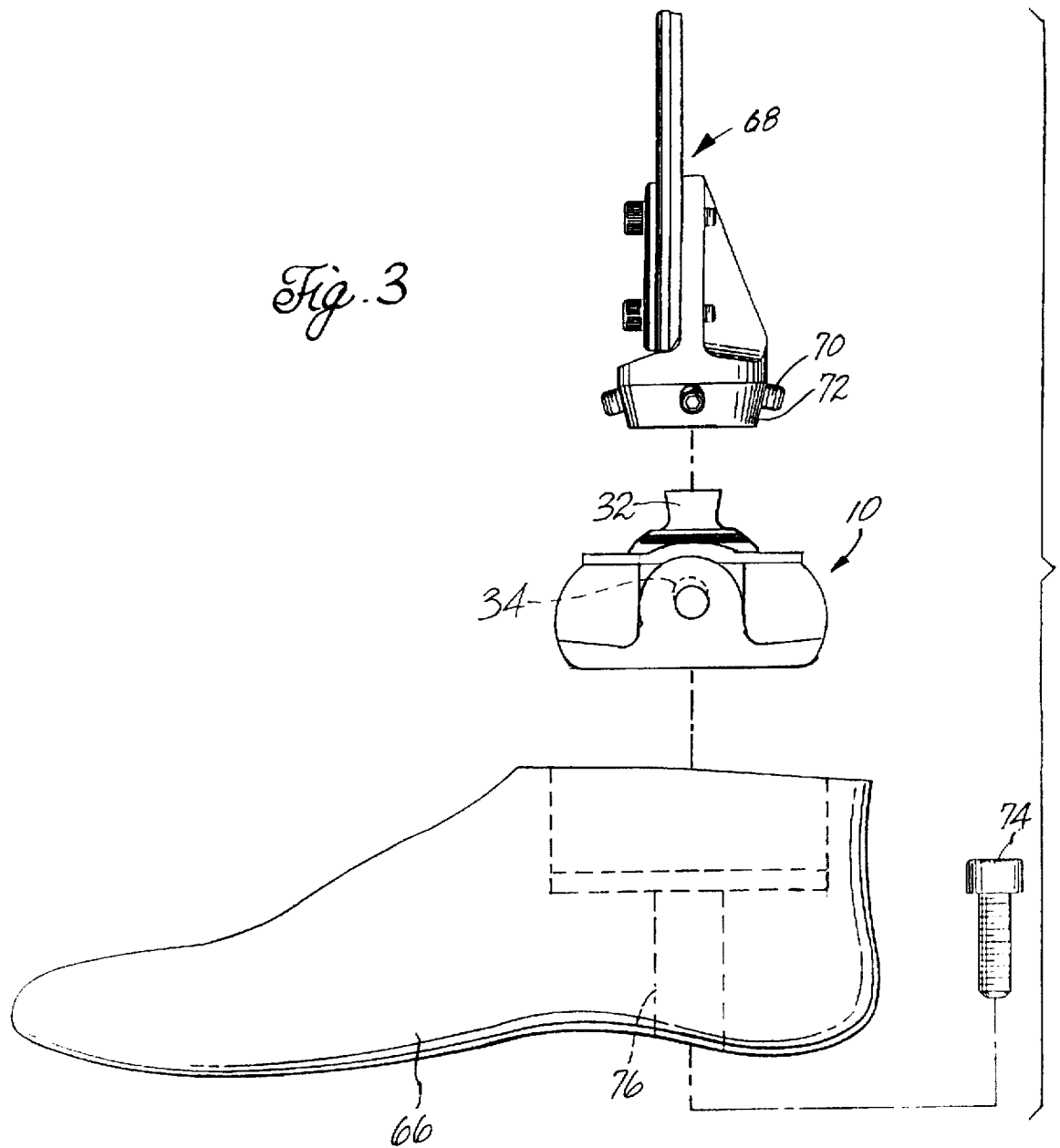
FIGS. 3 is an exploded side elevational view, showing the ankle joint of FIG. 1 incorporated into a below-knee prosthesis.

An assembled ankle joint is then positioned between a foot component 66 and a lower leg component 68 as shown in FIG. 3. The ankle joint 10 is attached to the lower leg component 68 such that the four angular sides of the boss 32 are contacted by separate set screws 70 which are carried at 90° intervals spaced apart around the bottom portion of a female socket 72. In use, the boss 32 can be inserted into the socket 72, and the set screws can be loosened or tightened and the boss moved into various angular configurations for providing angular adjustments between the ankle joint and the lower leg component 68. The ankle joint is also connected to the foot component 66 by a bolt 74 which passes through a hole 76 in the bottom of the foot component and into the threaded washer 50 of the ankle joint. By making the ankle joint a separate component, it is universally adaptable between most manufacturer's foot components and lower leg components.

The multi-axis ankle joint of the present invention provides dynamic foot motion allowing the foot to articulate in multiple axes providing plantar flexion, dorsiflexion, inversion, eversion, and vertical shock absorption motion.

Although the present invention has been described and is illustrated with respect to a preferred embodiment thereof, it is to be understood that it is not to be so limited, since changes and modifications may be made therein which are within the full and intended scope of this invention as hereinafter claimed.

What is claimed is:

1. A prosthetic ankle joint comprising:

a housing having a bottom portion and a top portion;

a front bumper and a rear bumper positioned within the housing between the bottom portion and the top portion;

a single pin passing through the front and rear bumpers for rigidly connecting the front and rear bumpers with the housing to provide multiple axis of movement of the ankle joint; and means for attaching the ankle joint between a foot component and a lower leg component.

2. The ankle joint of claim 1 wherein the bumpers are polyurethane and the front bumper has a shore hardness higher than the rear bumper.

3. The ankle joint of claim 1 wherein the ankle joint further comprises at least one flange on the bottom portion, on the top portion, on the front bumper, and on the rear bumper such that the flanges are overlapping and each containing an axially aligned hole for the passage of the pin.

4. The ankle joint of claim 3 wherein the hole in the flange on the upper portion of the housing is elongated.

5. The ankle joint of claim 1 wherein the means for attaching the ankle joint between the foot and the lower leg components comprises a threaded hole located in the bottom portion of the housing and a prosthetic link positioned on the top portion of the housing.

6. The ankle joint of claim 1 wherein the front and rear bumpers include a vertical chamber for receipt of a cylindrical limiter.

7. A prosthesis comprising:

a lower leg component;

a foot component; and a ankle joint comprising:

a housing having a bottom portion and a top portion;

a front bumper and a rear bumper positioned within the housing between the top portion and the bottom portion;

a single pin passing through the front and rear bumpers for rigidly connecting the front and rear bumpers with the housing to provide multiple axis of movement of the lower leg component; and means for attaching the ankle joint between the foot component and the lower leg component.

8. The ankle joint of claim 7 wherein the bumpers are polyurethane and the front bumper has a shore hardness higher than the rear bumper.

9. The ankle joint of claim 7 wherein the prosthesis further comprises at least one flange on the bottom portion, on the top portion, on the front bumper, and on the rear bumper such that the flanges are overlapping and each containing an axially aligned hole for the passage of the pin.

10. The ankle joint of claim 9 wherein the hole in the flange on the upper portion of the housing is elongated.

11. The ankle joint of claim 7 wherein the means for attaching the ankle joint between the foot and the lower leg components comprises a threaded hole located in the bottom portion of the housing and a prosthetic link positioned on the top portion of the housing.

12. The ankle joint of claim 7 wherein the front and rear bumpers include a vertical chamber for receipt of a cylindrical limiter.

* * * * *